(12) United States Patent
Mustafa et al.

(10) Patent No.: US 11,998,631 B2
(45) Date of Patent: Jun. 4, 2024

(54) DRY SHAMPOO MOUSSE COMPOSITION FOR HAIR

(71) Applicant: AMERICAN SPRAYTECH, L.L.C., North Branch, NJ (US)

(72) Inventors: Aaysha Mustafa, North Brunswick, NJ (US); Efeosa Jesuorobo, Newark, NJ (US)

(73) Assignee: American Spraytech, L.L.C., North Branch, NJ (US)

( * ) Notice: Subject to any disclaimer, the term of this patent is extended or adjusted under 35 U.S.C. 154(b) by 163 days.

(21) Appl. No.: 16/028,854

(22) Filed: Jul. 6, 2018

(65) Prior Publication Data

US 2019/0008751 A1    Jan. 10, 2019

Related U.S. Application Data

(60) Provisional application No. 62/529,062, filed on Jul. 6, 2017.

(51) Int. Cl.
| | | |
|---|---|---|
| *A61K 8/73* | (2006.01) | |
| *A61K 8/04* | (2006.01) | |
| *A61K 8/25* | (2006.01) | |
| *A61K 8/26* | (2006.01) | |
| *A61K 8/31* | (2006.01) | |
| *A61K 8/34* | (2006.01) | |
| *A61K 8/36* | (2006.01) | |
| *A61K 8/41* | (2006.01) | |
| *A61K 8/42* | (2006.01) | |
| *A61K 8/44* | (2006.01) | |
| *A61K 8/46* | (2006.01) | |
| *A61K 8/55* | (2006.01) | |
| *A61K 8/81* | (2006.01) | |
| *A61K 8/86* | (2006.01) | |
| *A61K 8/891* | (2006.01) | |
| *A61K 8/896* | (2006.01) | |
| *A61Q 5/02* | (2006.01) | |

(52) U.S. Cl.
CPC .............. *A61K 8/732* (2013.01); *A61K 8/046* (2013.01); *A61K 8/25* (2013.01); *A61K 8/26* (2013.01); *A61K 8/31* (2013.01); *A61K 8/34* (2013.01); *A61K 8/361* (2013.01); *A61K 8/416* (2013.01); *A61K 8/42* (2013.01); *A61K 8/44* (2013.01); *A61K 8/463* (2013.01); *A61K 8/466* (2013.01); *A61K 8/55* (2013.01); *A61K 8/8147* (2013.01); *A61K 8/86* (2013.01); *A61K 8/891* (2013.01); *A61K 8/896* (2013.01); *A61Q 5/02* (2013.01)

(58) Field of Classification Search
CPC . A61K 8/046; A61K 8/25; A61K 8/26; A61K 8/31; A61K 8/34; A61K 8/361; A61K 8/416; A61K 8/42; A61K 8/44; A61K 8/463; A61K 8/466; A61K 8/55; A61K 8/732; A61K 8/8147; A61K 8/896; A61K 8/86; A61K 8/891; A61Q 5/02

See application file for complete search history.

(56) References Cited

U.S. PATENT DOCUMENTS

| | | | |
|---|---|---|---|
| 3,912,665 A | 10/1975 | Spitzer et al. | |
| 4,035,267 A | 7/1977 | Gleckler et al. | |
| D402,890 S | 12/1998 | Guillemot | |
| 5,872,087 A | 2/1999 | Neelakantan | |
| D406,239 S | 3/1999 | Guillemot | |
| 2004/0258648 A1* | 12/2004 | Creamer | A61Q 5/12 424/70.16 |
| 2004/0265347 A1 | 12/2004 | Auguste | |
| 2006/0115504 A1 | 6/2006 | Loyen | |
| 2007/0066499 A1* | 3/2007 | Slavtcheff | A61Q 19/00 510/130 |
| 2009/0214628 A1 | 8/2009 | de Rijk | |
| 2014/0199255 A1* | 7/2014 | Sasik | A61K 8/85 424/70.9 |
| 2014/0283865 A1 | 9/2014 | Avery et al. | |
| 2015/0139917 A1 | 5/2015 | Gawtrey et al. | |
| 2016/0106634 A1 | 4/2016 | Gawtrey et al. | |
| 2016/0287484 A1 | 10/2016 | Neame | |
| 2016/0317396 A1 | 11/2016 | Perfitt et al. | |
| 2018/0000700 A1 | 1/2018 | Smail et al. | |

(Continued)

FOREIGN PATENT DOCUMENTS

| | | |
|---|---|---|
| WO | 9600563 A1 | 1/1996 |
| WO | 0012412 A1 | 3/2000 |

(Continued)

OTHER PUBLICATIONS

Sateesh Krishna Chand Chundru; "Effect of counter ion concentration added with mixture of water and ethylene glycol on Krafft temperature of sodium dodecyl sulfate"; Master's Thesis and Doctoral Dissertation; published Dec. 2007.*

Sneed; "What's Inside Dry Shampoo? Alcohol, Petroleum, and Clay"; Wired (www.wired.com/2015/05/whats-inside-dry-shampoo/); published online May 19, 2015.*

(Continued)

*Primary Examiner* — Jeffrey T. Palenik

(74) *Attorney, Agent, or Firm* — Renner, Kenner, Greive, Bobak, Taylor & Weber Co., LPA

(57) ABSTRACT

A dry shampoo composition is provided that is highly absorbent and light weight. The water-based composition may be formulated as an aerosol mousse. The aerosol mousse may be formed by combining a propellant and a mousse concentrate, and dispensing the combination from an aerosol dispenser. The dry shampoo mousse concentrate may include at least one sebum-absorbing powder, at least one cleansing surfactant, at least one anti-caking agent, at least one plasticizer, and at least a minimum amount of an aqueous solvent.

19 Claims, No Drawings

(56) References Cited

U.S. PATENT DOCUMENTS

2018/0153782 A1    6/2018   Desale
2018/0168986 A1    6/2018   Knappe et al.

FOREIGN PATENT DOCUMENTS

| WO | 03049711 A3 | 6/2003 | |
| --- | --- | --- | --- |
| WO | 2013143792 A2 | 10/2013 | |
| WO | 2013143935 A2 | 10/2013 | |
| WO | WO 2016/066730 A1 * | 5/2016 | ............... A61Q 5/02 |
| WO | 2016110578 A1 | 7/2016 | |

OTHER PUBLICATIONS

Nunez; "9 Things You Don't Know About Using Dry Shampoo"; Reader's Digest (www.rd.com/list/dry-shampoo/#:~:text=Unlike%20regular%20shampoo%2C%20which%20is,chemist%20and%20co%2Dfounder%20of); published online May 24, 2021.*

Herrwerth et al., "Highly Concentrated Cocamidopropyl Betaine—The Latest Developments for Improved Sustainability and Enhanced Skin Care" Tenside Surfactants Detergents 45 (2008) 6, 304-308.

Luck, et al., "Foods 3. Food Additives" Ullmann's Encyclopedia of Industrial Chemistry, 2012.

International Search Report for Application No. PCT/US2018/40996 dated Oct. 22, 2018.

* cited by examiner

DRY SHAMPOO MOUSSE COMPOSITION FOR HAIR

CROSS-REFERENCE TO RELATED APPLICATION

This application claims the benefits of U.S. Provisional Patent Application No. 62/529,062, filed Jul. 6, 2017, which is incorporated herein by reference.

FIELD OF THE INVENTION

One or more embodiments of the present invention relate to aerosol dry shampoo compositions for hair and dispensers and method of use thereof.

BACKGROUND OF THE INVENTION

The use of dry shampoos provide an alternative method for maintaining the cleanliness and appearance of hair without incurring the damaging effects of excessive washing in water. And, the use of a dry shampoo can save time and provide added convenience since no rinsing with water is needed.

Desirable characteristics of dry shampoo products include a satisfactory capacity to absorb oil, without a heavy feel or a tendency to form clumps of particles. It is also necessary for dry shampoo products to avoid leaving visible residues in the hair after cleaning. Improved dry shampoo compositions having these and other desirable characteristics are needed. Many current dry shampoo products leave a visible residue that must be removed by brushing or blotting it from the scalp. Improved dry shampoo compositions are needed that do not require brushing to remove the shampoo from the hair.

SUMMARY OF THE INVENTION

The present invention provides methods and compositions relating to a dry shampoo composition. One or more embodiments provides an aerosol mousse dry shampoo composition comprising starch, an anti-caking agent, and a propellant.

Other embodiments provide a method for shampooing hair. The method includes the steps of dispensing an aerosol mousse dry shampoo composition onto the hair, and distributing the composition onto the hair and scalp. Advantageously, the dry shampoo composition does not leave a visible powder or residue on the hair or scalp, and does not need to be removed.

In some embodiments, the dry shampoo composition may be essentially colorless and/or transparent following application to hair, and, in some embodiments, the dry shampoo composition may leave little or no colored residue on the hair. Such compositions may reduce or eliminate an oily and/or unaesthetic appearance of hair.

DETAILED DESCRIPTION OF ILLUSTRATIVE EMBODIMENTS

In one or more embodiments, a dry shampoo composition is provided that is highly absorbent and light. The water-based composition may be formulated as an aerosol mousse The aerosol mousse dry shampoo composition may be described in terms of two portions: the propellant, and all other ingredients. All ingredients other than the propellant may be referred to as a dry shampoo mousse concentrate. Accordingly, when discussing the effective amounts of components within the dry shampoo composition, the amounts may be stated based upon the mousse concentrate, and may also be stated based upon the total aerosol dry shampoo composition, i.e. including the propellant.

Propellant

In one or more embodiments, the aerosol dry shampoo composition includes a propellant. Propellants can be used individually or blended together. Advantageously, the selection of a propellant or blend of propellants may be used to achieve a particular spray pattern, control particle size, conform to government regulations, or for cost considerations.

Propellants may be selected from the group consisting of hydrocarbons, hydrofluorocarbons, ethers, and combinations thereof. Examples of hydrocarbon propellants include pentane, n-butane, isobutane, and propane. Examples of hydrofluorocarbon propellants include 1,1,1,2-tetrafluoroethane (134a) and 1,1-difluoroethane (152a). An example of an ether propellant includes dimethyl ether. In one or more embodiments, the propellant is a combination of butane and propane. Butane/propane propellants are commercially available, for example under the designation AB-46 from Aeropres. In one or more embodiments, the propellant is a combination of isobutane and propane. Isobutane/propane propellants are commercially available, for example under the trade name A-63.

In one or more embodiments, the propellant includes from about 20 to about 40 wt. % propane, in other embodiments, from about 30 to about 35 wt. % propane, based upon the total weight of propellant. In these or other embodiments, the propellant includes from about 50 to about 80 wt. % propane, in other embodiments, from about 60 to about 75 wt. % propane, based upon the total weight of propellant.

In one or more embodiments the total amount of propellant is from about 2 to about 97 wt. %, in other embodiments from about 4 to about 90 wt. %, and in other embodiments from about 5 to about 80 wt. %, based upon the total weight of the dry shampoo composition. In one or more embodiments the total amount of propellant is from about 2 to about 20 wt. %, in other embodiments from about 4 to about 15 wt. %, and in other embodiments from about 5 to about 10 wt. %, based upon the total weight of the dry shampoo composition.

Mousse Concentrate

"Mousse," for purposes herein, refers to an aerosolized, creamy foam. Mousse concentrate refers to a liquid composition that is capable of forming a mousse upon being dispensed from an aerosol dispenser. In one or more embodiments, the dry shampoo mousse concentrate is water-based. In one or more embodiments, the dry shampoo mousse concentrate is an emulsion. In one or more embodiments, the dry shampoo mousse concentrate includes at least one sebum-absorbing powder, at least one cleansing surfactant, at least one anti-caking agent, at least one plasticizer, and at least a minimum amount of an aqueous solvent.

Sebum-Absorbing Powder

The amount and type of the sebum-absorbing powder is not particularly limited, so long as the amount and type of powder is effective to form a stable dry shampoo mousse concentrate, and to absorb or adsorb the oily, waxy substance called sebum that is produced by human hair and scalp. Sebum-absorbing powders are more fully described in United States Patent Application Publication Nos. 2004/0265347 A1, 2006/0115504 A1, 2015/0139917 A1, and 2016/0106634 A1, which are incorporated by reference herein.

In one or more embodiments, the sebum-absorbing powder includes one or more starches. A starch material may function as an oil absorber. Non-limiting examples of starch materials include cornstarch, potato starch, tapioca starch, rice starch, wheat starch, and cassaya starch. A starch material may be modified or unmodified. A modified starch material is a starch which has been derivatized or altered by processes known to those of ordinary skill in the art, such as esterification, etherification, oxidation, acid hydrolysis, crosslinking, or enzyme conversion. Non-limiting examples of modified starch materials include aluminum starch octenylsuccinate, sodium starch octenylsuccinate, calcium starch octenylsuccinate, distarch phosphate, hydroxyethyl starch phosphate, hydroxypropyl starch phosphate, sodium carboxymethyl starch, and sodium starch glycolate. It should be understood, however, that in some embodiments, a starch material may be replaced by another oil-absorbing powder, for example, cellulose, chalk, talc, fullers earth, etc.

Suitable starches include corn starch, potato starch, tapioca starch, rice starch, wheat starch and cassava starch, and modifications and combinations thereof. In one or more embodiments, the sebum-absorbing powder includes one or more of rice starch and corn starch. In one or more embodiments, one or both of the rice starch and corn starch are surface-modified. In one or more embodiments, both rice starch and corn starch are present in the dry shampoo composition.

In one or more embodiments, the total amount of sebum-absorbing powder, based upon the total weight of the mousse concentrate, is from about 10 to about 50 wt. %, in other embodiments, from about 12 to about 40 wt. %, and in other embodiments, from about 14 to about 20 wt. %.

In one or more embodiments, where a dry shampoo composition is provided as an aerosol, the total percentage weight of the sebum-absorbing powder may be from about 10 to about 50 wt. %, in other embodiments, from about 12 to about 40 wt. %, and in other embodiments, from about 14 to about 20 wt. %, based upon the total weight of the aerosol dry shampoo composition.

In one or more embodiments, rice starch may be present in an amount of from about 10 to about 50 wt. %, based upon the total weight of the mousse concentrate. In other embodiments, rice starch may be present in an amount of from about 12 to about 40 wt. %, in other embodiments, from about 14 to about 20 wt. %, based upon the total weight of the mousse concentrate.

In one or more embodiments, rice starch may be present in an amount of from about 10 to about 50 wt. %, based upon the total weight of the aerosol dry shampoo composition. In other embodiments, rice starch may be present in an amount of from about 12 to about 40 wt. %, in other embodiments, from about 14 to about 20 wt. %, based upon the total weight of the aerosol dry shampoo composition.

In one or more embodiments, corn starch may be present in an amount of from about 0.1 to about 5 wt. %, based upon the total weight of the mousse concentrate. In other embodiments, corn starch may be present in an amount of from about 0.2 to about 4 wt. %, in other embodiments, from about 0.4 to about 1 wt. %, based upon the total weight of the mousse concentrate.

In one or more embodiments, corn starch may be present in an amount of from about 0.1 to about 5 wt. %, based upon the total weight of the aerosol dry shampoo composition. In other embodiments, corn starch may be present in an amount of from about 0.2 to about 4 wt. %, in other embodiments, from about 0.4 to about 1 wt. %, based upon the total weight of the aerosol dry shampoo composition.

Advantageously, other starches can be avoided. For example, in one or more embodiments, the amount of starch other than corn and rice starch is less than about 30 wt. %, in other embodiments, less than about 10 wt. %, in other embodiments, less than about 5 wt. %, in other embodiments, less than about 2 wt. %, in other embodiments, less than about 1 wt. %, in other embodiments, less than about 0.5 wt. %, and in other embodiments, less than about 0.1 wt. %, based upon the total weight of the mousse concentrate.

In one or more embodiments, the amount of starch other than corn and rice starch is less than about 30 wt. %, in other embodiments, less than about 10 wt. %, in other embodiments, less than about 5 wt. %, in other embodiments, less than about 2 wt. %, in other embodiments, less than about 1 wt. %, in other embodiments, less than about 0.5 wt. %, and in other embodiments, less than about 0.1 wt. %, based upon the total weight of the aerosol dry shampoo composition. In one or more embodiments, the dry shampoo composition is devoid of starch other than corn and rice starch.

Cleansing Surfactant

In one or embodiments, the composition comprises an anionic, nonionic, amphoteric or zwitterioninc cleansing surfactant.

Examples of suitable anionic cleansing surfactants include alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms, and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

In one or more embodiments, the anionic surfactant is an alkyl sulfate or alkyl ether sulfate. These materials have the respective formulae R2OSO3M and R1O (C2H4O) xSO3M, wherein R2 is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. In one or more embodiments, R2 has 12 to 14 carbon atoms, in a linear rather than branched chain.

Examples of anionic cleansing surfactants include sodium lauryl sulphate and sodium lauryl ether sulphate(n)EO, (where n is from 1 to 3); more preferably sodium lauryl ether sulphate(n)EO, (where n is from 1 to 3); most preferably sodium lauryl ether sulphate(n)EO where n=1.

In one or more embodiments, the level of alkyl ether sulphate is from about 0.5 wt % to about 25 wt %, based upon the total weight of the mousse concentrate, in other embodiments, from about 3 wt % to about 18 wt %, in other embodiments, from about 6 wt % to about 15 wt %, based upon the total weight of the mousse concentrate.

The total amount of anionic cleansing surfactant in compositions of the invention generally ranges from about 0.5 wt % to about 45 wt %, in other embodiments, from about 1.5 wt % to about 20 wt %, based upon the total weight of the mousse concentrate.

In one or more embodiments, compositions of the invention may contain one or more non-ionic surfactant. Examples of nonionic surfactants that may be included in compositions of the invention include condensation products of aliphatic (C8-C18) primary or secondary linear or branched chain alcohols or phenols with alkylene oxides, usually ethylene oxide and generally having from 6 to 30 ethylene oxide groups. Alkyl ethoxylates are particularly preferred. Most preferred are alkyl ethoxylates having the formula R—(OCH2CH2)nOH, where R is an alkyl chain of C12 to C15, and n is 5 to 9.

Other suitable nonionic surfactants include mono- or di-alkyl alkanolamides. Examples include coco mono- or di-ethanolamide and coco mono-isopropanolamide.

Further nonionic surfactants which can be included in compositions of the invention are the alkyl polyglycosides (APCs). Typically, APG is one which comprises an alkyl group connected (optionally via a bridging group) to a block of one or more glycosyl groups. Preferred APGs are defined by the following formula: RO-(G).sub.n wherein R is a branched or straight chain alkyl group which may be saturated or unsaturated and G is a saccharide group.

R may represent a mean alkyl chain length of from about C5 to about C20. Preferably R represents a mean alkyl chain length of from about C8 to about C12. Most preferably the value of R lies between about 9.5 and about 10.5. G may be selected from C5 or C6 monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants that may be included in compositions of the invention include the C10-C18 N-alkyl (C1-C6) polyhydroxy fatty acid amides, such as the C12-C18 N-methyl glucamides, as described for example in WO 92/06154 and U.S. Pat. No. 5,194,639, and the N-alkoxy polyhydroxy fatty acid amides, such as C10-C18N-(3-methoxypropyl) glucamide.

In one or more embodiments, non-ionic surfactant may be included in an amount ranging from about 0.1 to about 10 wt. %, in other embodiments, from about 0.5 wt % to about 8 wt %, in other embodiments, from about 1 wt. % to about 4 wt. %, based upon the total weight of the mousse concentrate.

In one or more embodiments, non-ionic surfactant may be included in an amount ranging from about 0.1 to about 10 wt. %, in other embodiments, from about 0.5 wt % to about 8 wt %, in other embodiments, from about 1 wt. % to about 4 wt. %, based upon the total weight of the aerosol composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

In one or more embodiments, the amphoteric or zwitterionic surfactant is cocamidopropyl betaine.

Mixtures of any of the foregoing amphoteric or zwitterionic surfactants may also be suitable. In one or more embodiments, mixtures of cocamidopropyl betaine with further amphoteric or zwitterionic surfactants may be employed. In one or more embodiments, the further amphoteric or zwitterionic surfactant is sodium cocoamphoacetate. In one or more embodiments, the cleansing surfactant may be selected from ceteareth-25, cocamidopropyl betaine, and mixtures thereof.

In one or more embodiments, amphoteric or zwitterionic surfactant may be included in an amount ranging from about 0.1 to about 10 wt. %, in other embodiments, from about 0.25 wt % to about 8 wt %, in other embodiments, from about 0.5 wt. % to about 5 wt. %, in other embodiments, from about 0.7 wt. % to about 4 wt. %, based upon the total weight of the mousse concentrate.

In one or more embodiments, amphoteric or zwitterionic surfactant may be included in an amount ranging from about 0.1 to about 10 wt. %, in other embodiments, from about 0.25 wt % to about 8 wt %, in other embodiments, from about 0.5 wt. % to about 4 wt. %, based upon the total weight of the aerosol composition.

Anti-Caking Agent

In some embodiments, a dry shampoo composition comprises at least one type of anti-caking agent. An anti-caking agent may aid in oil absorption and/or act as a suspending agent. An anti-caking agent may be modified, for example, to include organic moieties. Such a modification may increase the dispersion of the anti-caking agent in the solvent, as compared to a non-modified version the clay, may reduce or eliminate the static charge on the product, and/or may aid in the binding of the sebum absorber to hair. Those of ordinary skill in the art will be aware of methods and techniques for modifying an anti-caking agent, such as with organic groups. Non-limiting examples of classes of anti-caking agents include bentonite, hectorite, kaolin, and anti-adherents such as magnesium stearate, and combinations thereof. Non-limiting examples of modified bentonites and hectorites include stearalkonium hectorite, stearalkonium bentonite, quaternium-18 bentonite, and quaternium-18 hectorite, and combinations thereof. In one embodiment, the anti-caking agent is selected from stearalkonium hectorite, magnesium stearate, and combinations thereof.

In one or more embodiments, the mousse concentrate includes at least about 0.05 wt. %, in other embodiments, at least about 0.1 wt. %, and in other embodiments, at least about 0.15 wt. %, total anti-caking agent, based upon the total weight of the mousse concentrate. In these or other embodiments, the mousse concentrate includes no more than about 10 wt. %, in other embodiments, no more than about 5 wt. %, and in other embodiments, no more than about 1 wt. %, total anti-caking agent, based upon the total weight of the mousse concentrate.

In one or more embodiments, the mousse concentrate includes from about 0.05 to about 10 wt. %, in other embodiments, from about 0.1 to about 8 wt. %, and in other embodiments, from about 0.2 to about 5 wt. %, total anti-caking agent, based upon the total weight of the mousse concentrate.

In embodiments where a dry shampoo composition is provided as an aerosol, the total wt. % of the anti-caking agent may be from about 0.01 to about 10 wt. %, in other embodiments, from about 0.05 to about 8 wt. %, and in other embodiments, from about 0.1 to about 5 wt. %, based upon the total weight of the aerosol dry shampoo composition.

Plasticizer

In one or more embodiments, the dry shampoo composition includes at least one plasticizer. Non-limiting examples of plasticizers include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In or more embodiments, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof. In one or more embodiments, the plasticizer is selected from dimethicone copolyols, which are sometimes referred to as PEG dimethicones and PPG dimethicones. In one or more embodiments, the plasticizer is PEG-12 dimethicone.

Aqueous Carrier

In some embodiments, a dry shampoo composition comprises an aqueous carrier. In one or more embodiments, the mousse concentrate includes from about 30 to about 70 wt. % water, in other embodiments, from about 35% to about 68 wt. %, in other embodiments, from about 40 to about 65 wt. %, based upon the total weight of the mousse concentrate.

In embodiments where a dry shampoo composition is provided as an aerosol, the total wt. % of the water may be from about 30 wt. % to about 70 wt. %, in other embodiments, from about 35% to about 68%, in other embodiments, from about 40% to about 65 wt. %, based upon the total weight of the aerosol dry shampoo composition.

In one or more embodiments, to reduce the time required for the hair to become dry after application of the shampoo composition, one or more volatile alcohols may be added. Volatile alcohols include C1-6 alcohols, such as methanol, ethanol, propanol, butanol, pentanol, and hexanol, and isomers thereof. In one or more embodiments, the mousse concentrate may include up to about 45 wt. % of one or more volatile alcohols, in other embodiments, up to about 42 wt. %, in other embodiments, up to about 40 wt. %, in other embodiments, up to about 35 wt. %, in other embodiments, up to about 30 wt. %, based upon the total weight of the mousse concentrate. In one or more embodiments, the mousse concentrate may include up to about 20 wt. % of one or more volatile alcohols, in other embodiments, up to about 15 wt. %, in other embodiments, up to about 10 wt. %, in other embodiments, up to about 5 wt. %, in other embodiments, up to about 1 wt. %, based upon the total weight of the mousse concentrate.

In embodiments where a dry shampoo composition is provided as an aerosol, the mousse concentrate may include up to about 48 wt. % of one or more volatile alcohols, in other embodiments, up to about 45 wt. %, in other embodiments, up to about 40 wt. %, in other embodiments, up to about 35 wt. %, in other embodiments, up to about 30 wt. %, based upon the total weight of the mousse concentrate. In one or more embodiments, the total percentage weight of the volatile alcohols may be up to about 25 wt. %, in other embodiments, up to about 20 wt. %, in other embodiments, up to about 10 wt. %, in other embodiments, up to about 5 wt. %, in other embodiments, up to about 1 wt. %, based upon the total weight of the aerosol dry shampoo composition.

Advantageously, the amount of organic carrier may be limited. Organic carriers include volatile hydrocarbons and silicones. Volatile silicone compounds generally have an atmospheric pressure boiling point of less than about 220° C., or between about 50° C. and about 220° C., and contain between about 3 and about 7 silicon atoms. Non-limiting examples of volatile silicone compounds include polydimethylsiloxanes (e.g., having a viscosity less than about 5 cSt at 25° C.), cyclomethicone, cyclohexane siloxane, decamethyltetrasiloxane, octamethyltrisiloxane, decamethylpentasiloxane, decamethylcyclopentasiloxane, octamethylcyclotetrasiloxane, trimethylsilylamodimethicone, phenyl trimethicone, hexamethyidisiloxane, dimethylsiloxane/methylalkylsiloxane, or combinations thereof.

In one or more embodiments the mousse concentrate includes less than about 20 wt. % of the non-aqueous organic carrier material, in other embodiments, less than about 15 wt. %, in other embodiments, less than about 10 wt. %, in other embodiments, less than about 5 wt. %, in other embodiments, less than about 1 wt. %, based upon the total weight of the mousse concentrate.

In embodiments where a dry shampoo composition is provided as an aerosol, the total percentage weight of the non-aqueous organic carrier material may be less than about 25 wt. %, in other embodiments, less than about 20 wt. %, in other embodiments, less than about 10 wt. %, in other embodiments, less than about 5 wt. %, in other embodiments, less than about 1 wt. %, based upon the total weight of the aerosol dry shampoo composition.

Optional Ingredients

In some embodiments, the dry shampoo composition may comprise at one or more optional ingredients. Non-limiting examples of additive components include: antioxidants; essential oils; perfumes; waxes; emulsifiers such as fatty alcohols, including cetearyl alcohol, emulsion stabilizers such as stearyl alcohol, fillers; hair-fixative polymers; deodorizing agents; pediculicides; anti-dandruff agents; cosmetic and/or dermatological active agents including emollients, moisturizers, vitamins (e.g., vitamin B complexes (e.g., including thiamine, nicotinic acid, biotin, pantothenic acid, choline, riboflavin, vitamin B6, vitamin B12, pyridoxine, inositol, carnitine), vitamins A, C, D, E, K and their derivatives (e.g., vitamin A palmitate) or pro-vitamins), essential fatty acids, sunscreens, herb and/or plant extracts (e.g., aloe); dispersing or suspending agents (e.g., silica); pharmaceutically active agents (e.g., poly(2-hydroxystearic acid); anti-static agents (e.g., tricetyl methyl ammonium chloride); pearlescent aids (e.g., such as coated mica, ethylene glycol distearate); opacifiers (e.g., tin); preserving agents (e.g., 1,2-dibromo-2,4-dicyano butane, benzyl alcohol, methyl paraben, propyl paraben, imidazolidinyl urea); coloring agents or dyes; odor neutralizers; preservatives (e.g., phenoxyethanol); and sequestering agents; or combinations thereof.

In one or more embodiments, the dry shampoo composition may include one or more conditioning agents. Examples of conditioning agents include cationic conditioning polymers, silicones, hydrocarbon oils, fatty esters, and combinations thereof. Conditioning agents are further described in U.S. Patent App. Pub. Nos. 2011/0081392 A1 and 2006/0135382 A1. In one or more embodiments, the dry shampoo composition includes one or more of PPG-3 isostearyl methyl ether, caprylic/capric triglyceride, diisopropyl adipate, polyquaternium-4, lauryl methyl gluceth-10 hydroxypropyldimonium chloride, cetrimonium chloride, and acrylates/C12-22 alkyl methacrylate copolymer.

In one or more embodiments, the dry shampoo composition may include a deodorizing agent. Non-limiting examples of deodorizing agents include cyclodextrins, zinc undecylenate, undecylenic acid, citronellyl methylcrotonate, natural fragrance oils, and combinations thereof.

The amount of each optional ingredient is not particularly limited. Generally, one of ordinary skill in the art can determine the effective amount of each optional ingredient. Typically, the effective amount of an optional ingredient will be from about 0.01% to about 10 wt. %, in other embodiments, from about 0.01% to about 5 wt. %, in other embodiments, from about 0.1% to about 3 wt. %, in other embodiments, from about 0.01% to about 1 wt. %, in other embodiments, from about 0.1% to about 5 wt. %, in other embodiments, from about 1% to about 5 wt. %, based upon the total weight of the mousse concentrate.

Typically, the effective amount of an optional ingredient will be from about 0.01 to about 10 wt. %, in other embodiments, from about 0.01 to about 5 wt. %, in other embodiments, from about 0.1 to about 3 wt. %, in other embodiments, from about 0.01% to about 1 wt. %, in other embodiments, from about 0.1% to about 5%, in other embodiments, from about 1% to about 5 wt. %, based upon the total weight of the aerosol dry shampoo composition.

In some embodiments a composition of the present invention does not comprise additional components which may leave a colored residue on the hair. For example, the composition may not comprise talc, chalk, or other compounds known to leave a white residue. In some cases, the composition does not comprise magnesium stearate and/or rice protein. In embodiments where a composition comprises a low amount of starch material (e.g., less than about 8%), the composition may comprise an increased amount of clay material (e.g., up to about 10%). An increased amount of a clay material such as stearalkonium hectorite may help to balance and replace some of the oil-removal efficacy that may be lost by a low amount of starch material.

Method of Preparation

The mousse concentrate preparation is not particularly limited. In one or more embodiments, a two-part preparation method is employed, wherein an aqueous pre-mix is prepared, a non-aqueous pre-mix is prepared, and then the aqueous pre-mix and non-aqueous pre-mix are combined and mixed until a homogeneous emulsion is obtained. If desired, additional ingredients may be added to the emulsion.

In one or more embodiments, the aqueous pre-mix is prepared under standard conditions of temperature and pressure. In one or more embodiments, one or more solid ingredients may be liquefied at elevated temperature, and then added to the non-aqueous pre-mix. In one or more embodiments. The non-aqueous pre-mix may be heated to about 160 degrees F., in order to liquefy and/or solubilize all of the ingredients in the non-aqueous pre-mix.

In one or more embodiments, the aqueous pre-mix and oil phase pre-mix are combined and mixed under standard conditions of temperature and pressure. In embodiments where one or more ingredients are heated to elevated temperatures in order to liquefy and/or solubilize those ingredients, further processing steps may also be conducted at elevated temperatures.

In one or more embodiments, the following procedure may be employed:

Procedure:
1. Prepare the aqueous pre-mix by adding one or more water-soluble film formers and/or viscosity modifiers to water, with mixing. Slowly sift in the ingredients, trying to avoid adding any large lumps. Mix until dissolved.
2. Add one or more water-soluble conditioning agents, and mix until a clear solution is obtained.
3. Separately, prepare the non-aqueous pre-mix by combining the water-insoluble ingredients. Waxy ingredients may be pre-heated to liquefy them prior to addition to the non-aqueous pre-mix. If desired, the non-aqueous pre-mix may be heated to about 160 F. In one or more embodiments, one or more water-insoluble conditioning agents, one or more cleansing surfactants, and one or more emulsion stabilizers are combined, with mixing, until a homogeneous solution or emulsion is obtained.
4. To the non-aqueous pre-mix is added one or more anti-caking agents and one or more sebum-absorbing materials, and the combination is mixed until the anti-caking agent(s) and sebum-absorber(s) are well dispersed.
5. The non-aqueous pre-mix is added to the aqueous pre-mix and homogenized. 6. Additional ingredients may be added, if desired.

The mousse concentrate and propellant may be combined to prepared the aerosol dry shampoo composition using any suitable technique, as will be known to those of ordinary skill in the art. In some cases, the aerosol dry shampoo composition may be prepared by mixing an appropriate amount of a liquefied gaseous propellant and a mousse concentrate under pressure, followed by packing the mixture in an aerosol container. In other cases, an aerosol container may be loaded with a mousse (e.g., as a powder, slurry, or liquid), followed by pressurizing the container with a propellant and sealing the container.

Aerosol Dispenser

Advantageously, the dry shampoo compositions of the present invention may be dispensed as an aerosol mousse. Therefore, the present invention provides an aerosol dispensing system. The aerosol dispensing system is not unduly limited, and may generally be described as having a container that includes an outlet and is capable of being pressurized, a valve system, and an actuator.

An aerosol container may be formed of any suitable material, for example, metal (e.g., aluminum), glass, plastic, or combinations thereof. In most embodiments, the aerosol container is formed essentially of metal. The container may comprise a dip tube and/or a spray nozzle. Examples of mousse delivery devices are further described in International Patent App. Pub. No. WO 2000/012412 A1, U.S. Design Pat. Nos. D406239 and D402890, all of which are incorporated herein by reference.

Although there are many types of valve systems and actuators that are suitable to dispense the aerosol dry shampoo compositions of the present invention, exemplary valve systems include those available from Lindal Valve Co. In one or more embodiments, the valve system includes a stem valve provided by Lindal under the moniker CA39F. In one or more embodiments, the actuator includes a full-cup actuator provided by Lindal under the moniker ST340A.

In one or more embodiments, the orifice through which the product is dispensed has an opening having a diameter of at least about 0.025 inches.

Method of Use

The compositions of the invention may be used for topical application to hair, in particular, when the hair has become greasy due to an accumulation of sebum. The dry shampoo compositions of the present invention may be utilized conventionally. An effective amount of the dry shampoo composition may be applied to hair, preferably dry hair. In some cases, the application of the shampoo may encompass massaging or working the shampoo in the hair such that all or most of the hair proximate the scalp is contacted. The term "effective amount," as used herein, is an amount which is effective in improving the appearance of the hair (e.g., reducing oil content or improving aesthetics).

The dry shampoo compositions may be useful in settings where a subject does not have access to or may not be exposed to water (e.g., wilderness trips, or hospitals), and/or to preserve and/or add body to a hairstyle without the need for washing the hair. Advantageously, dry shampoo compositions, following application to hair, are transparent, or substantially transparent. That is, the dry shampoo compositions do not leave a colored residue or flakes. Moreover, the compositions of the present invention do not weigh-down the hair, and leave little or no residue. There is no residue that has to be removed by brushing, blotting, or wiping, in contrast to other dry shampoo products.

The dry shampoo composition may be used by a subject a plurality of times, with no soap and water wash in between uses.

In one or more embodiments, the dry shampoo compositions of the present invention are effective to soften and/or plasticize styling resins, such that the hair can be easily combed and/or restyled.

It should be understood that the compositions and methods of the present invention may be employed on any mammal that has hair or fur. Generally, the invention is directed toward use with humans.

In order to demonstrate the practice of the present invention, the following example has been prepared and tested. The examples should not, however, be viewed as limiting the scope of the invention. The claims will serve to define the invention.

EXAMPLE

Example 1

A dry shampoo mouse concentrate was prepared by combining:

| INGREDIENT | TRADE NAME | SUPPLIER |
|---|---|---|
| Water | | |
| Corn Starch Modified | Amaze | Akzo Nobel |
| PEG-12 Dimethicone | Xiameter OFX-0193 Fluid | Nexo (Dow Corning) |
| PPG-3 Isostearyl Methyl Ether | Arlamol LST | Croda |
| Caprylic/Capric Triglyceride | Jeechem CTG | Jeen |
| Ceteareth-25 | Brij CS25 | Croda |
| Stearyl Alcohol | Stearyl Alcohol | Jeen |
| Isopropyl Myristate | Bentone GEL IMP V | Elementis Specialties |
| Stearalkonium Hectorite | | |
| Propylene Carbonate | | |
| *Oryza Sativa* (Rice) Starch | D.S.A 7 | Argana Starke GmbH |
| Cetrimonium Chloride | | |
| Water | Hydrosal Hairoma Therapy | Salvona |
| Fragrance | | |
| Polyvinyl Alcohol | | |
| Acrylates/C12-22 Alkyl Methacrylate Copolymer | | |
| Phenoxyethanol | | |
| Caprylic/Capric Triglyceride | Apiscalp | Croda |
| *Apium Graveolens* (Celery) Seed Extract | | |
| Tocopheryl Acetate | Vitamin E Acetate | Protameen |
| Phenoxyethanol | Jeecide Phenoxy | Jeen |
| Diisopropyl Adipate | Hallstar DIPA | The Hallstar Co. |

The dry shampoo mousse concentrate was aerosolized with a propellant that is a combination of butane and propane, available under the trade name AB-46 from Aeropres, to form an aerosol dry shampoo composition. Notably, when the same or similar mousse concentrate was aerosolized with A-63 (blend of isobutane and propane), and dispensed from the same type of dispenser, improved dryness of the foam structure was observed.

Various modifications and alterations that do not depart from the scope and spirit of this invention will become apparent to those skilled in the art. This invention is not to be duly limited to the illustrative embodiments set forth herein.

What is claimed is:

1. A dry shampoo mousse concentrate comprising:
    a sebum-absorbing rice starch, where the total amount of the sebum-absorbing rice starch, based upon the total weight of the mousse concentrate, is from about 10 to about 50 wt. %,
    from about 0.1 to about 10 wt. % total cleansing surfactant selected from the group consisting of alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, alkyl ether carboxylic acids and salts thereof, alkyl ethoxylates, alkyl alkanolamides, alkyl polyglycosides, alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, and mixtures thereof, at least one anti-caking agent, at least one plasticizer, and from about 30 to about 70 wt. % water, all based upon the total weight of the mousse concentrate.

2. The dry shampoo mousse concentrate of claim 1, where the anti-caking agent is selected from the group consisting of bentonite, hectorite, magnesium stearate, kaolin, and mixtures thereof.

3. The dry shampoo mousse concentrate of claim 1, where the total amount of anti-caking agent is from about 0.05 to about 10 wt. %, based upon the total weight of the mousse concentrate.

4. The dry shampoo mousse concentrate of claim 1, where the plasticizer is selected from the group consisting of polyols, copolyols, polycarboxylic acids, polyesters, dimethicone copolyols, and mixtures thereof.

5. The dry shampoo mousse concentrate of claim 1, where the concentrate further comprises a C1-6 alcohol selected from the group consisting of methanol, ethanol, propanol, butanol, pentanol, and hexanol, and mixtures thereof, and where the amount of the C1-6 alcohol is up to about 45 wt. %, based upon the total weight of the mousse concentrate.

6. The dry shampoo mousse concentrate of claim 1, where the concentrate comprises from about 0.5 to about 4 wt. % cleansing surfactant, based upon the total weight of the mousse concentrate.

7. The dry shampoo mousse concentrate of claim 1, wherein the concentrate is devoid of talc, chalk, white pigments, and colorants.

8. An aerosol mousse composition for simultaneously removing sebum and hair styling resins from hair, the composition comprising:

a mousse concentrate and a propellant, where the mousse concentrate comprises:

a sebum-absorbing rice starch, where the total amount of the sebum-absorbing rice starch, based upon the total weight of the mousse concentrate, is from about 10 to about 50 wt. %, from about 0.1 to about 10 wt. % total cleansing surfactant selected from the group consisting of alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, alkyl ether carboxylic acids and salts thereof, alkyl ethoxylates, alkyl alkanolamides, alkyl polyglycosides, alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, and mixtures thereof, at least one anti-caking agent, at least one plasticizer, and from about 30 to about 70 wt. % water, all based upon the total weight of the mousse concentrate, wherein the aerosol mousse composition functions to remove sebum and hair styling resins when applied to hair.

9. The aerosol mousse composition of claim 8, where the propellant is selected from the group consisting of blends of propane and butane, and blends of propane and isobutene.

10. The aerosol mousse composition of claim 8, where the cleansing surfactant is selected from the group consisting of alkyl betaines, alkyl amidopropyl betaines, and mixtures thereof.

11. The aerosol mousse composition of claim 8, where the anti-caking agent is selected from the group consisting of bentonite, hectorite, magnesium stearate, kaolin, and mixtures thereof.

12. The aerosol mousse composition of claim 8, where the total amount of anti-caking agent is from about 0.05 to about 10 wt. %, based upon the total weight of the mousse concentrate.

13. The aerosol mousse composition of claim 8, where the plasticizer is selected from the group consisting of polyols, copolyols, polycarboxylic acids, polyesters, dimethicone copolyols, and mixtures thereof.

14. The aerosol mousse composition of claim 8, where the concentrate further comprises a C1-6 alcohol selected from the group consisting of methanol, ethanol, propanol, butanol, pentanol, and hexanol, and mixtures thereof, and where the amount of the C1-6 alcohol is up to about 45 wt. %, based upon the total weight of the mousse concentrate.

15. The aerosol mousse composition of claim 8, where the composition comprises from about 0.1 to about 4 wt. % cleansing surfactant, based upon the total weight of the aerosol mousse composition.

16. The aerosol mousse composition of claim 8, wherein the mousse concentrate consists of the rice starch, cleansing surfactant, anti-caking agent, plasticizer, water, and optionally one or more of the following:

antioxidants, essential oils, perfumes, waxes, emulsifiers, emulsion stabilizers, fillers, deodorizing agents, pediculicides, anti-dandruff agents, emollients, moisturizers, vitamins, essential fatty acids, sunscreens, herb extracts, plant extracts, dispersing agents, suspending agents, pharmaceutically active agents, antistatic agents, pearlescent aids, opacifiers, preserving agents, coloring agents, dyes, odor neutralizers, preservatives, and sequestering agents, and combinations thereof.

17. The aerosol mousse composition of claim 8, wherein the composition leaves no visible residue when applied to hair or scalp.

18. The aerosol mousse composition of claim 8, wherein the mousse concentrate consists of the rice starch, cleansing surfactant, anti-caking agent, plasticizer, water, and optionally one or more of C1-6 alcohols, deodorizing agents, preservatives, and combinations thereof.

19. A dry shampoo mousse concentrate consisting of:

a sebum-absorbing rice starch, where the total amount of the sebum-absorbing rice starch, based upon the total weight of the mousse concentrate, is from about 10 to about 50 wt. %, from about 0.1 to about 10 wt. % total cleansing surfactant selected from the group consisting of alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, alkyl ether carboxylic acids and salts thereof, alkyl ethoxylates, alkyl alkanolamides, alkyl polyglycosides, alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, and mixtures thereof, at least one anti-caking agent,
at least one plasticizer,
from about 30 to about 70 wt. % water, all based upon the total weight of the mousse concentrate, and
optionally one or more of the following: antioxidants, essential oils, perfumes, waxes, emulsifiers, emulsion stabilizers, fillers, deodorizing agents, pediculicides, anti-dandruff agents, emollients, moisturizers, vitamins, essential fatty acids, sunscreens, herb extracts, plant extracts, dispersing agents, suspending agents, pharmaceutically active agents, anti-static agents, pearlescent aids, opacifiers, preserving agents, coloring agents, dyes, odor neutralizers, preservatives, and sequestering agents, and combinations thereof.

* * * * *